United States Patent [19]

Stone

[11] Patent Number: 4,489,097
[45] Date of Patent: Dec. 18, 1984

[54] INTRAVENOUS SOLUTIONS WITH ANTIMICROBIAL AGENT

[75] Inventor: Roger L. Stone, Fairfield, Ohio

[73] Assignee: The Procter & Gamble Company, Cincinnati, Ohio

[21] Appl. No.: 396,542

[22] Filed: Jul. 8, 1982

Related U.S. Application Data

[63] Continuation of Ser. No. 918,532, Jun. 23, 1978, abandoned, which is a continuation-in-part of Ser. No. 816,625, Jul. 18, 1977, abandoned, which is a continuation-in-part of Ser. No. 709,342, Jul. 28, 1976, abandoned.

[51] Int. Cl.³ .................. A61K 31/20; A61K 31/19; A61K 37/00
[52] U.S. Cl. .................. 424/318; 424/177; 424/317
[58] Field of Search ............ 424/177, 317, 318

[56] References Cited

U.S. PATENT DOCUMENTS

| | | | |
|---|---|---|---|
| 3,404,987 | 10/1968 | Kooistra et al. | 99/150 |
| 3,743,519 | 7/1973 | Haas | 99/159 |
| 3,767,803 | 10/1973 | Nurnberg | 424/263 |
| 3,873,720 | 3/1975 | Suzuki et al. | 424/312 |

OTHER PUBLICATIONS

*Remington's Pharmaceutical Sciences,* 13th ed. Mack Publishing Co. Easton, Pa. (1965), pp. 501–502.
*Ann. Surg.,* Sep., 1972, pp. 265–272.
Doctoral Dissertation of R. L. Stone–p. 37.
*Antibiotics and Chemotherapy,* vol. V, No. 5 (May, 1955), pp. 255–262.
*Chemical Abstracts,* vol. 75 (1971):95737f.
Georges, *Arch. Belges. Derm. Syph.* 9/1:1–13 (1953).

*Primary Examiner*—Frederick E. Waddell
*Attorney, Agent, or Firm*—Steven J. Goldstein; Jacobus C. Rasser; Jerry J. Yetter

[57] ABSTRACT

Antifungal/antibacterial materials are added to sterile compositions intended for administration to humans or lower animals to minimize bacterial and mycotic contamination which can cause infections associated with the medical and veterinary use of such compositions.

2 Claims, No Drawings

INTRAVENOUS SOLUTIONS WITH ANTIMICROBIAL AGENT

CROSS REFERENCE TO RELATED APPLICATION

"This is a continuation of application Ser. No. 918,532, filed June 23, 1978, now abandoned which is a continuation-in-part of application Ser. No. 816,625, filed July 18, 1977, now abandoned which is a continuation-in-part of application Ser. No. 709,342, filed July 28, 1976, now abandoned."

BACKGROUND OF THE INVENTION

The present invention encompasses compositions used in the medical and veterinary sciences. In particular, intravenous compositions, especially those used for parenteral nutrition, are improved by coadministration with antifungal/antibacterial agents.

Fungi and bacteria are ubiquitous. Fortunately, most bacteria and fungi remain non-pathogenic to humans and lower animals unless they somehow become introduced into the bloodstream of lymphatic system. However, once internalized, massive infestation throughout the body can result. Bacterial sepsis can usually be treated successfully with antibiotics, although a complete treatment regimen can be expensive and time consuming. Moreover, bacterial strains which are resistant to antibiotics are becoming a serious problem. Mycotic (fungal, mold, yeast) infections, which are typically occasioned by extremely high fevers, are unusually refractive to standard therapeutic agents used to combat bacterial infections and often result in death of the patient.

Intravenous administration of solutions of various types to humans and lower animals is required in the treatment of a variety of disease states. Yet, the risk of bacterial or mycotic contamination and sepsis is especially acute during i.v. therapy. It is now becoming widely recognized that prolonged administration of intravenous solutions, which involves repeated changes of exhausted solution reservoirs, removal and re-insertion of catheters, and other physical manipulations and adjustments of the intravenous apparatus, can lead to whole body mycotic and/or bacterial contamination and infections if sterile conditions are not rigorously maintained. Recent investigations have demonstrated that bacterial or fungal contaminants are present in many supposedly sterile i.v. solutions being used in hospitals.

Physicians have long decried the fact that progress in developing new treatment regimens for burn victims, comatose patients, patients who have undergone gastrointestinal surgery, cancer victims, and other patients who require intravenous feeding is being hindered by the problem of sepsis. The following references illustrate the current state of the medical art in this area.

"Infection is a significant hazard, and disseminated fungal infection has been a particularly frequent and dread complication of total parenteral nutrition."—Goldmann and Maki, "Infection Control in Total Parenteral Nutrition", *Journal of American Medical Association*, 223, 12 (1973), pp. 1360–64.

"Disseminated candidiasis is an increasingly common cause of morbidity and death, especially in hospital patients . . . "—Letter to the Editor, *The Lancet*, Nov. 13, 1976, p. 1084.

At least 10,000,000 hospital patients receive i.v. therapy yearly. Septicemia rates as high as 8% are seen in some hospitals.—Maki, "Preventing Infection in Intravenous Therapy", *Hospital Practice*, April, 1976, pp. 95–104.

"On the clinical front the approach to infection with yeasts is far less purposeful; and this is well illustrated by Candida, which is evidently an increasingly common cause of morbidity and death, especially in hospital patients."—"Troublesome Candida", *The Lancet*, July 26, 1975, at 167.

*C. albicans* was identified as the causative microbial species in 8 of 13 cases of parenteral septicemia.—Curry and Quie, "Fungal Septicemia in Patients Receiving Parenteral Hyperalimentation", *NEJM*, 285, 22 (1971), pp. 1221–25.

The likelihood that unused i.v. devices are contaminated is small. "However, once they are in use, contamination is another matter. The 35 percent contaminations [in this study] suggest that this complication may occur with ease."—Duma, et al., "Septicemia from Intravenous Infusions", *NEJM*, 284, 5 (1971), pp. 257–60.

" . . . [T]he indwelling catheter which is necessary for the delivery of the concentrated glucose solution . . . may be a route by which direct contamination can occur." [456]—Ashcraft and Lepe, "Candida Sepsis Complicating Parenteral Feeding", *JAMA*, 212, 3 (1970), pp. 454–46.

Seventy-four hospital i.v. needles tested; 24 were infested with microorganisms, including Candida; infestation increased with increasing duration of needle placement.—Lowenbraun, et al., "Infection from Intravenous 'Scalp-Vein' Needles in a Susceptible Population", *JAMA*, 212, 3 (1970), pp. 451–53.

Seven-month period; 3 patients on i.v. develop secondary bloodstream infection originating from the site of catheter insertion; 2 die.—Darrell and Garrod, "Secondary Septicaemia from Intravenous Cannulae", *British Medical Journal*, May 24, 1969, pp. 481–82.

Amphotericin to treat Candida in i.v. therapy.—Brennan, et al., "Prolonged Parenteral Alimentation: Candida Growth and the Prevention of Candidemia by Amphotericin Instillation", *Ann. Surg.*, 172, Sept. 1972, p. 265.

"The risks [of i.v. feeding] appear unacceptably high . . . can hyperalimentation be made safe?—It is unfortunate that answers are not available."—Editorial, *NEJM*, 285, 22 (1971), pp. 1258–59.

So patients sicken and die, not because the manufacturers of intravenous solutions are negligent, but because once the product passes from the skilled, sophisticated hands of the specialist to the hands of a possibly indifferent, less well educated, overworked hospital employee, manipulative problems and inattention to detail lead to massive infection.

Physicians are currently meeting this problem by curtailing, or even discontinuing, prolonged use of i.v. feeding. They recognize that, once the patient does become infected, the normal treatment regimen for the patient's original illness must be interrupted to fight the hospital-induced infection with a potent antibiotic and, if the patient somehow survives that, only then can treatment of the patient's original problem be resumed.

The present invention is based on the discovery that certain carboxylate antimicrobial agents solve the dual problems of mycotic and bacterial sepsis associated with the use of i.v. solutions. It is to be understood that the use of carboxylate anitmicrobials in the manner of this invention is prophylactic (i.e., to prevent mycotic or bacterial contamination which could result in infection) rather than therapeutic (i.e., to cure an established disease).

When properly used, the preferred carboxylates disclosed herein are so effective that they can constitute at least a partial substitute for the heat- or filtration-sterilization procedures normally used in the manufacture of intravenous solutions, and the like, with the added advantage that the carboxylates maintain sterility even during use situations where sterility can be lost.

RELATED REFERENCES

The use of antimicrobials to inhibit the growth of bacteria, fungi and molds in food compositions is well known. For example, sodium propionate is routinely added to commercial bread to inhibit mold. In spite of the body of literature on this general topic, workers in the medical/veterinary sciences do not appear to have appreciated the special benefits which are afforded when carboxylate antimicrobials are used in the manner of the present invention. This is indeed surprising, in light of the pressing need to avoid microbial contamination and possible sepsis in patients undergoing treatment regimens where there is any likelihood of direct contact between the blood or lymphatic fluids and the external environment.

Perhaps medical science has not fully recognized that newer medical techniques such as total parenteral nutrition have put patients at risk of sepsis.

Perhaps physicians have tacitly assumed that sterilized solutions secured from a reputable manufacturer will remain sterile in use, even under the suboptimal conditions which often face personnel in a busy hospital.

perhaps the thought that hazardous, complex antimicrobials would be required to maintain sterility in i.v. solutions has dissuaded manufacturers from conducting research in this area.

Or, perhaps the carboxylates have simply been passed over as seemingly ineffective antimicrobials in light of recent literature. For example, in May of 1975, J. J. Kabara, Ph.D., conducted a reexamination of nontoxic antimicrobial agents of the carboxylate type; Kabara: "Lipids as safe and effective antimicrobial agents for cosmetics and pharmaceuticals" *Cosmetics and Perfumery* Vol. 70 21 (1975). Dr. Kabara's work included a study of the antimicrobial activity of some fifteen fatty acids against various bacteria and the fungus *Candida albicans*. Dr. Kabara's data indicated that neither caproic (hexanoic) nor caprylic (octanoic) acid were inhibitory to any of the microorganisms under the test conditions. Yet, properly used in the manner disclosed herein, these two carboxylate materials have now been found to be particularly potent, yet safe and highly preferred antimicrobial agents.

The Doctoral Dissertation of the inventor herein, Roger L. Stone, entitled, The Requirements for Metabolizable Energy and Nitrogen for Maintenance in Parenterally Fed Sheep, The Ohio State University, published August, 1975, p. 37, discloses the use of propionic acid in intravenous solutions.

U.S. Pat. No. 2,154,449, to Hoffman, et al., 1939, describes the use of aliphatic carboxylic acids ($C_3$-$C_{12}$) or their salts as mold inhibitors in foods. The patent teaches the use of these acids to protect materials susceptible to mold, including tobacco, paper, leather, textiles, etc.

U.S. Pat. No. 2,190,714, to Hoffman, et al., 1940, claims a method of inhibiting mold growth in food products other than margarine and sourdough bread by adding a $C_3$-$C_{12}$ carboxylic acid thereto.

U.S. Pat. No. 3,404,987, to Kooistra and Troller, 1968, discloses and claims an antimicrobial composition containing 110 parts by weight of an edible mineral salt (iron, manganese, zinc, tin or silver) and 1-150 parts by weight of an edible acid preservative substance, specifically including propionic acid. The metal salts are taught to impart enhanced and sustained antimicrobial/antifungal activity to the acid preservative substance.

U.S. Pat. No. 1,772,975, Wieland, 1930, teaches the use of solutions of lactic acid, acetic acid, or homologs thereof, as antiseptics at properly adjusted pH's.

U.S. Pat. No. 2,466,663, Russ, et al., 1949, describes the use of caprylic (octanoic) acid to combat mycotic infections or growths. This acid may be used topically as a liquid, ointment or powder for the treatment of surface infections. It is also taught to be useful for combating internal infections by injecting, intravenously, solutions of the acid and its salts at the pH of blood.

The Merck Index, Seventh Edition, page 1117, teaches that zinc propionate is used as a fungicide on adhesive tape to reduce plaster irritation caused by molds, fungi and bacterial action. MERCK, at page 860, teaches that propionic acid, and propionates, e.g., sodium, zinc and calcium propionates, are used as mold inhibitors and preservatives and as topical fungicides in the form of ointments or powders.

Mycotic infections associated with the administration of intravenous solutions are generally attributed to some species of Candida, especially *C. albicans*. The effect of various fungistats on Candida has been reported in the literature.

The inhibition of the growth of *C. albicans* in vitro by propionic acid has been reported by Carpenter, Antibiotics and Chemotherapy V, No. 5, May, 1955, 255, 259.

Propionates and butyrates have been injected into animals in metabolic studies and for the relief of hyperglycemia conditions. B. J. Potter, Nature, No. 4326, 9/27/52 at 541 and R. M. Cook, *Biochim. et Biophys. Acta*, 201 (1970) 91-100.

A comparison of the bacteriostatic and fungistatic properties of propionic acid and caprylic acid was made by A. Georges, *Arch. belges. Derm. Syph.* 1953, 9/1 (1-13), who concluded that the fungistatic properties of the latter compound are greater than the former.

French Brevet Special de Medicament 8.058M, July, 1970, Application No. 148,347, Apr. 17, 1968, Jean-Pierre Durlach, discloses vitamin $B_6$ compositions containing magnesium propionate, magnesium lactate, and propionic acid to adjust pH. The compositions are said to be useful orally or parenterally for vitamin $B_6$ therapy.

The use of the natural body metabolite, propionate, as a fungistat in intravenous solutions is disclosed in the copending application of R. L. Stone, the inventor herein, Ser. No. 709,341, filed July 28, 1976.

The preferred octanoate antimicrobial agent herein appears on the food GRAS list for use at low levels in various areas of food processing and packaging.

SUMMARY OF THE INVENTION

The present invention is based on the discovery that, when used in the manner disclosed herein, certain carboxylate compounds kill a broad spectrum of microorganisms, and do so quite rapidly. Because they are safe to animal tissue, yet kill pathogens essentially on contact, the carboxylates can be used to maintain the sterility of sterilized compositions under the typical use situations which face medical and veterinary workers.

In the practice of this invention, carboxylates are used to kill, among others, the following types of microbial pathogens which are known to be associated with infusion-related septicemia in hospitals: Candida species; *Staphylococcus aureus;* Klebsiella species; Enterobacter species including *E. cloacae;* Serratia species; Pseudomonas species; *Streptococcus feacalis.* These pathogens are among those recognized by the Center for Disease Control as being important causative agents for sepsis in most hospitals.

Quite low concentrations of the most preferred carboxylate compounds used in the manner of the present invention kill the foregoing pathogens. Accordingly, the compositions provided by this invention can be administered to humans or lower animals without undesirable side effects which might be associated with the use of higher concentrations of less effective antimicrobials.

Perhaps most importantly, the carboxylate antimicrobials kill pathogenic microorganisms quickly. Thus, even when inadvertently introduced into sterile solutions during use, the pathogens are disposed of by the carboxylate before they are transmitted into the patient's bloodstream.

DETAILED DESCRIPTION OF THE INVENTION

The present invention encompasses compositions comprising: (1) a first agent selected from pharmaceutically-acceptable electrolytes, nutritive substances, and mixtures thereof, said electrolytes and nutritive substances being suitable for use in blood or serum; and (2) a second agent comprising a safe and effective amount of a $C_4$–$C_9$ carboxylate antimicrobial agent as disclosed hereinafter. The balance of the compositions as used comprises pyrogen-free water. The compositions herein are characterized by an in-use pH of about 6.0, or below, generally in the range of about 3.5 to about 5.8, most preferably in the pH range of about 3.5 to about 5.2. Within this critical acidic pH range, proper concentrations of the carboxylate compounds in the free acid form quickly and efficiently kill a wide variety of bacteria and fungi, including those reported by the Center for Disease Control as being common, troublesome hospital pathogens.

The compositions herein are useful for all purposes where contact between electrolyte solutions or nutrient solutions and blood or internal organs or systems is required, e.g., as plasma expanding agents, as the fluid medium in kidney dialyzers, as irrigation solutions for cleansing wounds, as respirator solutions, and the like. The present compositions are especially adapted for administration intravenously to humans or lower animals.

The special advantages of the present invention are of particular importance in the field of parenteral nutrition. The invention thus encompasses improved compositions and processes for providing parenteral nutrition to a human or lower animal in need of such treatment, with minimal incidence of bacterial or mycotic contamination and ensuing infection. The nutritive compositions herein are administered intravenously to provide a nutritious amount of a nutritive substance to the patient and are suitable for use over a prolonged treatment regimen. The total nutritional requirements of the patient can be met in this manner, even over a prolonged time span.

By "nutritious amount" herein is meant an amount of a material sufficient to support or sustain life, i.e., to feed.

By "nutritive substance" herein is meant a food substance which contributes to the metabolic requirements of a human or lower animal. More particularly, the nutritive substances herein comprise energy sources such as sugars; nitrogen sources such as proteins, polypeptides, amino acids, or mixtures thereof, which are commonly found in protein hydrolysates; and mixtures of sugars and nitrogen sources. Various commercially available lipid dispersions approved by the government for intravenous administration are not suitable for use herein, since lipids somehow interfere with the antimicrobial activity of the carboxylates. Moreover, albumin and other materials such as polyvalent cations which bind the carboxylic acids used herein can interfere with antimicrobial activity. Accordingly, when such interfering materials are present in the compositions of this invention, additional carboxylic acid must be used in the manner disclosed hereinafter to account for carboxylate which is lost due to such binding/interference. Vitamins and minerals can optionally be present in the nutritive compositions of this invention.

By "sugar" herein is meant the saccharidic materials which can be metabolized by humans and lower animals and employed as an energy source. Dextrose is highly preferred for this use.

By "amino acid source" or "nitrogen source" herein is meant any nutritive protein, polypeptide, amino acid, or protein hydrolysate which is sufficiently water soluble to be incorporated in nutritious amounts in an aqueous solution intended for i.v. administration.

By "fungi" herein are meant the higher protists, including the phycomycetes, the ascomycetes and basidiomycetes, as well as other protista commonly referred to as "yeasts" or "molds". Candida, especially *Candida albicans,* comprises a particular class of fungi which are a major medical problem associated with the prolonged use of intravenous solutions and which can be successfully combated by the practice of the present invention.

By "mycotic infection" herein is meant a disease state (especially candidiasis) within the human or lower animal organism caused by the direct introduction of fungi, molds or yeasts into the bloodstream.

The terms "bacteria" and "bacterial infection" are used herein in their usual context. As will be seen hereinafter, the carboxylate compounds, properly used, are unexpectedly effective for controlling both gram positive and gram negative bacteria.

By "pharmaceutically acceptable" herein is meant materials which are suitable for administration, especially i.v., to the blood or serum of humans or lower animals in the amounts specified herein at an acceptable benefit/risk ratio, according to the precepts of sound medical practice.

By "water-soluble" herein is meant soluble at the concentrations disclosed, under typical use conditions.

By "antimicrobial agent" herein is meant a $C_4$–$C_9$ carboxylate material which quickly kills microorganisms, including various bacteria, molds, fungi and yeasts, thereby preventing their establishment, growth, and proliferation in the present compositions, and thus preventing contamination of the human or animal patient. Examples of such carboxylate antimicrobials are disclosed in more detail, hereinafter.

By "electrolyte solution" herein is meant aqueous solutions of at least about 0.1% of a pharmaceutically-acceptable, water-soluble sodium salt, potassium salt (especially NaCl and KCl), calcium salt, magnesium salt, or acetate, lactate or phosphate salt, and the like, or mixtures thereof, at concentrations commonly used in i.v., irrigation, respirator and/or dialysis solutions and in solutions such as "Ringer's", and the like.

By the term "safe and effective amount" herein is meant an amount of the $C_4$–$C_9$ carboxylate antimicrobial agent which comprises at least the minimum lethal concentration (MLC, as described more fully hereinafter) of the particular $C_4$–$C_9$ agent being used, or some multiple of the MLC, not to exceed an amount which is compatible with the compositions and safe for administration to a patient.

By the term "comprising" herein is meant that various other, compatible, water-soluble ingredients can be present in the compositions of this invention as long as the critical carboxylate antimicrobial agent is present. The term "comprising" thus encompasses and includes the more restrictive terms "consisting of" and "consisting essentially of" used to characterize the essential materials used herein. As disclosed above, the compositions herein are formulated to be substantially free from amounts of albumin and lipids which interfere with the antimicrobial efficacy of the carboxylates.

All percentages herein are by weight, unless otherwise specified.

CARBOXYLATE ANTIMICROBIALS

The antimicrobial agents used herein are selected from the non-aromatic water-soluble $C_4$–$C_9$ alkyl, alkenyl or alkynyl organic acids, or mixtures thereof, or any of their water-soluble, pharmaceutically-acceptable salts. Such salts include, for example, the common water-soluble sodium, potassium, ammonium, etc., salts. The sodium and potassium salts are preferred.

While various carboxylate compounds exhibit different degrees of antimicrobial activity in the practice of this invention, the water-soluble n-alkyl $C_4$, $C_5$, $C_6$, $C_7$, $C_8$, and $C_9$ carboxylates exhibit excellent antimicrobial activity. The n-hexanoic and n-octanoic acids and pharmaceutically-acceptable, water-soluble salts thereof are much preferred for use herein, due to their ease of use and their broad spectrum antimicrobial activity and speed of kill in solution. The hexanoate and octanoate antimicrobials are highly preferred, with n-octanoate being most highly preferred, inasmuch as these materials in their free acid form rapidly kill essentially all important gram positive and gram negative pathogens, and Candida, at low solution concentrations in the acid pH range disclosed herein.

It has now been discovered that the microbiocidal activity of the $C_4$–$C_9$ carboxylate antimicrobials used herein is directly related to the presence of their respective free acids in solution. The concentration of free carboxylic acid in solution, as opposed to carboxylate salt (anionic) form, is a function of the pH of the solution. The carboxylic acid salts can be used herein, but only as long as the pH of the solution is in the acid range so that the minimum lethal concentration (MLC) of free acid is present. Accordingly, the amount of acid or acid salt used will vary somewhat with the use pH. The amount of a given acid salt or acid which will provide the MLC at a given pH will depend on the pKa of the acid. Of course, knowing the pKa, the MLC of the particular acid and the solution pH, the amount of any $C_4$–$C_9$ acid or acid salt to be used is easily calculated. For example, with the sodium octanoate antimicrobial the relationship between pH, concentration of sodium salt and percentage of free acid in solution is as follows.

TABLE 1

| pH  | % Sodium Octanoate | Concentration of Free Acid |
|-----|--------------------|----------------------------|
| 5.4 | 0.251              | 3.5 millimolar (mM)        |
| 4.8 | 0.107              | 3.5 mM                     |
| 4.4 | 0.078              | 3.5 mM                     |
| 4.0 | 0.066              | 3.5 mM                     |
| 3.6 | 0.061              | 3.5 mM                     |

Microbial testing with n-octanoic acid using the screening criteria disclosed hereinafter has shown that a concentration of about 3 millimolar is the MLC for this acid. The above table specifies the amount of sodium octanoate needed to achieve the MLC of octanoic acid in solution over a range of pH's. Of course, concentrations of free acid higher than the MLC can be used.

In like manner, using the MLC's of n-butyric, n-pentanoic, n-hexanoic, n-heptanoic and n-nonanoic acids, together with their pKa's, the amounts of their respective salts required to provide an MLC for each antimicrobial, at any desired solution pH, can be mathematically determined. The MLC values (based on the criteria disclosed hereinafter) for these acids are as follows: $C_4$ (0.4 molar); $C_5$ (0.11M); $C_6$ (30 mM); $C_7$ (9 mM); $C_9$ (1 mM).

As can be seen from the MLC values, the amounts of the $C_4$ and $C_5$ acids needed to provide a minimum lethal concentration in solution are substantially higher than for the more preferred $C_6$–$C_9$ carboxylic acids. Likewise, at any pH, the concentration of the salts of the $C_4$ and $C_5$ acids needed to reach the free acid MLC will be correspondingly higher than with the $C_6$–$C_9$ acid salts. Since the compositions herein are often used with critically ill patients, it may be important not to overburden the body with excessive amounts of the carboxylates; hence, the $C_4$ and $C_5$ compounds are less preferred than the $C_6$–$C_9$ compounds. Likewise, the $C_7$ and $C_9$ compounds may not be as easily metabolized due to their having an odd number of carbon atoms and are thus less preferred than the even chain $C_6$ and $C_8$ compounds. As between the $C_8$ and $C_6$ compounds, n-octanoate is prefered over n-hexanoate simply because $C_8$ is more effective (MLC 3 mM vs. MLC 30 mM).

Carboxylates above $C_9$, e.g., decanoates, undecanoates, etc., are not useful herein inasmuch as these compounds either are not compatible with the nutritive substances used herein in solution, or precipitate from solution on storage at cool temperatures.

ANTIMICROBIAL TESTING

Antimicrobial testing was carried out by exposing test microorganisms to various concentrations of antimicrobial agents for short periods of time followed by plating on appropriate media. Screening criteria for selecting suitable antimicrobial agents were as follows:
1. Cell dose
One log below visual turbidity
($10^4$ to $10^5$ organisms per ml)
2. Time of exposure to the test antimicrobial agent
Thirty seconds to 5 minutes;

3. Concentration of the test antimicrobial agent
Use of the lowest concentration which satisfies the above two criteria;
4. Test solution
Use of an i.v. solution which will support or sustain the metabolism and/or growth of microorganisms;
5. Use of metabolically compatible antimicrobial agents at a physiologically-acceptable pH; and
6. Use of antimicrobial agents which are compatible with the other ingredients of the i.v. or electrolyte solutions.

It was judged extremely important that the antimicrobial agent kill the test organisms quickly, thereby assuring that the sterility of even those solutions which might be contaminated in use would be promptly and automatically re-established.

It was also judged important that any antimicrobial agent used in i.v. and irrigation solutions must provide a broad spectrum of kill, due to the variety of microorganisms which have been implicated as causative agents in hospital sepsis.

Surprisingly, many compounds reported in the literature as having significant antimicrobial, or "preservative", activity did not perform particularly well at lower concentrations when measured in laboratory tests using the foregoing criteria. Included among these agents were: acetic acid, propionic acid, n-butyric acid (the least preferred of the carboxylates herein), valeric acid, decanoic acid, undecanoic acid, dodecanoic acid, pivalic acid, iso-hexanoic acid, crotonoic acid, 6-aminohexanoic acid, suberic acid, adipic acid, sorbic acid, undecylenic acid, methyl gallic acid, propyl gallic acid, and the methyl, ethyl, propyl and butyl parabens compounds known in the art as preservatives.

In contrast with the foregoing, sodium n-octanoate (pH 5.3) gave the results appearing in Table 2 when tested using the foregoing criteria. As can be seen, the n-octanoate killed all test organisms within 1.5 minutes; substantially all organisms within 1 minute; and greater than 90% of all organisms within 0.5 minutes of contact.

TABLE 2
PERCENT OF INOCULUM VIABLE AFTER MIXING WITH 0.2% SODIUM OCTANOATE

| Organism Tested | Time of Exposure (min.) | | | | |
|---|---|---|---|---|---|
| ($10^4$ to $10^5$ per ml) | 0.5 | 1.0 | 1.5 | 2.0 | 2.5 |
| Candida albicans | 0.0 | 0.0 | 0.0 | 0.0 | 0.0 |
| Staphylococcus aureus | 6.1 | 0.005 | 0.0 | 0.0 | 0.0 |
| Streptococcus faecalis | 0.4 | 0.009 | 0.0 | 0.0 | 0.0 |
| Klebsiella pneumoniae | 2.5 | 0.005 | 0.0 | 0.0 | 0.0 |
| Serritia marcescens | 0.002 | 0.0 | 0.0 | 0.0 | 0.0 |
| Escherichia coli | 2.0 | 0.03 | 0.0 | 0.0 | 0.0 |
| Salmonella enteritidis | 2.0 | 0.06 | 0.0 | 0.0 | 0.0 |
| Pseudomonas flourescens | 0.002 | 0.0 | 0.0 | 0.0 | 0.0 |
| Pseudomonas aeruginosa | 0.02 | 0.0 | 0.0 | 0.0 | 0.0 |

SOLUTIONS

One type of nutritive solution encompassed by this invention comprises a water-soluble sugar as the nutritive substance. Any sugar which can be metabolized and utilized by a human or lower animal as an energy source can be employed in such solutions, but dextrose (i.e., glucose) is typically used. Listings of suitable metabolizable sugars appear in standard textbooks.

Dextrose solutions containing an MLC of the antimicrobial $C_4$-$C_9$ acids can be administered intravenously to humans or lower animals in the treatment of: dehydration; shock; collapse; ketosis of dairy cattle; pregnancy toxemia of sheep; treatment of poisoning by carbon tetrachloride, chloroform and other compounds toxic to the liver; hypoglycemia in piglets, cattle, ewes, dogs; for nutritional purposes; for temporary increases in blood volume; for diabetic coma (together with insulin); for hyperinsulinism; for diuresis in pulmonary edema and increased intracranial pressure; as a sclerosing agent for varicose veins; and in other standard medical therapies employing dextrose solutions. In general, dextrose is administered intravenously as a 5%-50% solution. Volumes up to several liters, or more, may be administered, as required. Standard reference textbooks describe in detail the concentration of dextrose solution typically administered intravenously in the management of various disease states.

Another type of nutritive solution encompassed by this invention comprises a water-soluble, metabolically-available, nitrogen source as the nutritive substance. In particular, water-soluble amino acid sources, especially sources of the essential amino acids, are used herein. Such materials include, for example, water-soluble acid and base hydrolysates of animal and vegetable proteins; water-soluble polypeptides, either natural or synthetic; and the amino acids, themselves, either in the form of free acids or their water-soluble, pharmaceutically-acceptable salts. The foregoing types of nutritive substances are commercially available and can be modified, in well-known fashion, to improve or adjust their nutritive properties, according to the nutritional requirements of the individual patient.

Nutritive solutions of the foregoing type typically comprise from about 0.5% to about 30%, preferably from about 1% to about 20%, of the nitrogen source.

Another type of nutritive solution encompassed by this invention comprises a sugar energy source and a water-soluble, metabolically-available nitrogen source as a mixed nutritive composition. Such solutions comprise a substantially complete dietary replacement for intravenous administration to humans or lower animals in need of such treatment. The sugars and nitrogen sources disclosed hereinabove are used in such solutions.

Other types of solutions where the present invention can be employed to advantage are the electrolyte solutions commonly used as irrigants, as kidney dialysis solutions, and as parenteral solutions which are administered i.v. to restore electrolyte balance in the bodies of humans and lower animals. Such solutions commonly contain from about 1% to about 15% NaCl, KCl, $MgCl_2$ or mixtures thereof.

Surprisingly, electrolyte solutions can be a source of bacterial and/or fungal contamination and sepsis in the hospital. While bacteria and fungi do not grow well in pure electrolyte solutions since there is no ready source of nitrogen or energy, neither are such microorganisms killed by electrolytes. Thus, if an electrolyte solution becomes contaminated, viable microorganisms can be introduced into the bloodstream where they can proliferate. The carboxylates effectively kill pathogenic microorganisms in electrolyte solutions when used at or above the carboxylate MLC in the acidic pH range disclosed above.

PREFERRED MODE

The compositions of this invention can be manufactured under conditions, and using manufacturing procedures, well known in the pharmaceutical field. The protein hydrolysates, saline solutions, sugar solutions, and the like, used in the practice of this invention are all known in the industry. The compositions herein can be conveniently prepared by simply dissolving sufficient carboxylate salt in the solution to provide at least an MLC of the free acid which corresponds to the salt. As required, the pH of the solution can be adjusted to the range disclosed herein. Standard acetate buffers or other pharmacologically-acceptable buffers can be used for this purpose. The solutions are then packaged in standard fashion and sterilized.

For convenience in use, the carboxylic acids or carboxylate salts, especially n-octanoates, can be packaged in unit dosage amounts especially designed for mixing with commercially available i.v. nutrient or saline solutions on site, immediately prior to use. The unit dosage amounts are, of course, based on the volume and concentration of the i.v. solution being treated. For most purposes, i.v. solutions are packaged in one-liter bottles to which is added about 0.61 g to about 10 g. (0.061–1%) of sodium octanoate, depending on pH, as disclosed above. This is conveniently done by injecting a concentrated aqueous solution of sodium n-octanoate from a sterile ampoule through the rubber septum in the neck of the i.v. bottle. Thus, the present invention encompasses, as an article of manufacture, a sterile ampoule with injection means (e.g., a hypodermic needle) containing a unit dose of a $C_4$–$C_9$ carboxylic acid or pharmaceutically-acceptable salt thereof, especially n-octanoic acid or salt thereof.

Pharmacologically-acceptable buffers (standard phosphate buffers, for example) can be packaged with the carboxylate to ensure that the final pH of the solution is in the range of 3.5 to 6.0, thus providing optical antimicrobial activity.

Preferred sterile solutions for total parenteral nutrition which can easily be prepared on site comprise: at least about 3 mM (preferably 0.1% to 1%; higher concentrations are not necessary; lower are useful, but activity is pH dependent, so lower concentrations are sub-optimal and are preferably not used since the chances of sepsis are increased unnecessarily) by weight of n-octanoic acid; from about 1% to about 20% by weight of a water-soluble amino acid source, especially protein hydrolysates; from about 5% to about 50% by weight of dextrose; the balance of said solution comprising pyrogen-free water, all at a preferred pH of from 4.9 to 5.2.

As noted, solutions encompassed by this invention can be prepared on site by simply dissolving an effective amount of the antifungal/antibacterial carboxylate in a pre-formed solution of the nutritive substance or electrolyte in pyrogen-free water, buffered as needed. Many amino acid and/or protein hydrolysate solutions are self-buffering at the pH range 4.9 to 5.2 associated with optimal antimicrobial activity of the carboxylates. In the alternative, the compositions are manufactured and maintained in a closed, sterile container until time of use. Additional sterilization of nutrient solutions comprising carboxylate antimicrobials and sugar can be carried out using heat or filtration techniques well known in the art. Solutions comprising the carboxylate antimicrobials and an amino acid source can likewise be further sterilized by heat or filtration. However, when mixtures of sugars and amino acid sources comprise the nutritive substance, it is preferable to avoid heat sterilization, inasmuch as chemical reactions between sugars and amino acids can occur; accordingly, it is preferable to use filtration techniques to sterilize such solutions. Under these latter circumstances, the added protection afforded by the addition of the carboxylate antimicrobial agents herein is substantial and contributes importantly to the safety of such products.

The compositions herein are used according to standard medical techniques. It will be appreciated that the process provided by this invention constitutes an improvement in the time-honored method for administering a nutrient solution or dispersion intravenously to humans or lower animals, said improvement comprising admixing with said solution or dispersion a safe and effective amount of a carboxylate antimicrobial agent, especially n-octanoic acid, or a pharmaceutically-acceptable, water-soluble salt thereof, at a pH which provides sufficient concentration of free acid for microbiocidal activity, prior to or concurrently with said administration, whereby a decreased incidence of mycotic and bacterial infection is secured.

Conveniently, the present i.v. process is carried out using compositions of the type disclosed hereinabove. Alternatively, the water-soluble antimicrobial agent can be packaged and used separately from the nutritive or electrolyte solution and introduced thereto during the course of intravenous feeding. It will also be appreciated that the administration of i.v. nutrients can be carried out by administering the solutions of sugar, amino acids, saline, etc., separately from each other to help provide the appropriate nutritional balance for the patient. Under such circumstances, the nutrient solutions can contain the antimicrobial carboxylate agent, or the agent can be separately packaged for co-administration through the same apparatus in the manner described above. Accordingly, the process herein is not limited to the use of the disclosed compositions, although such use is most convenient. Rather, the antimicrobial agent can be introduced continuously into the intravenous solution during i.v. administration to the patient. This is done at a point in the i.v. apparatus such that the carboxylate antimicrobial is in contact with the i.v. solution for 1 to 1.5 minutes, or more, prior to entry into the patient's bloodstream.

The following examples illustrate the practice of this invention.

EXAMPLE I

A dextrose solution (pH 5.0) suitable for intravenous administration is prepared by dissolving the following ingredients in pyrogen-free water.

| Ingredient | Amt/Liter |
| --- | --- |
| Sodium Chloride | 2.92 g. |
| Sodium Acetate | 2.722 g. |
| Potassium Chloride | 1.118 g. |
| Potassium Dihydrogen Phosphate | 1.361 g. |
| Magnesium Chloride | 0.355 g. |
| Calcium Borogluconate | 2.40 g. |
| Anhydrous Dextrose | 346.8 g. |
| n-Octanoic Acid | 0.65 g. |
| Trace Mineral Solution* | 1 ml |

*Zinc chloride 416 mgs, copper sulfate 156 mgs, manganese sulfate 61.3 mgs, sodium iodide 6.6 mgs, in 100 ml of distilled $H_2O$.

The solution of Example I is filtered and bottled under sterile conditions and is suitable for administration to humans and lambs, i.v., for a prolonged period of time with a decreased incidence of mycotic and bacterial infection, even though repeated manipulations of the i.v. apparatus occur.

In the composition of Example I the n-octanoic acid is replaced by the following acids, at the respective concentrations: n-hexanoic (30 mM); n-heptanoic (9 mM); and n-nonanoic (1.0 mM). Excellent results are secured.

EXAMPLE II

The composition of Example I is modified by replacing the octanoic acid with 1.3 g/l of: sodium n-octanoate and potassium n-octanoate, respectively, and excellent results are secured.

EXAMPLE III

A dextrose solution substantially similar to that of Example I is admixed (1:1) with a nitrogen source comprising a solution of commercial protein hydrolysate (AMINOSOL—modified fibrin hydrolysate, Abbott Laboratories, N. Chicago, Ill.), to provide a solution suitable for total parenteral nutrition. A ratio of 3.0 mg. of $N_2$ per infused Kcal. of energy is used. The n-octanoic acid is adjusted to a solution concentration of 4.5 mM (1.5×MLC); pH 5.1.

A solution prepared in the foregoing manner is suitable for the total parenteral nutrition of humans or lower animals for an extended period, by intravenous administration, with a reduced incidence of mycotic and bacterial infection occasioned by such use.

EXAMPLE IV

In the solution of Example III, the n-octanoic acid is replaced by 0.75 g/l of sodium n-octanoate and potassium n-octanoate, respectively, to provide solutions useful for i.v. administration to humans or lower animals.

EXAMPLE V

A solution of protein hydrolysate suitable for prolonged intravenous administration to humans or lower animals with a decreased incidence of mycotic infection is as follows.

| Ingredient | Wt. % |
|---|---|
| Soybean Protein Hydrolysate* | 5 |
| Sodium n-Octanoate | 0.2 |
| Sodium Chloride | 1.0 |
| Pyrogen-free Water** | Balance |

*Water-soluble acid hydrolysate, neutralized to pH 5.6 with NaOH
**Solution self-buffered to pH 4.95.

The solution of Example V is prepared by dissolving the ingredients in the water and is sterilized by heating. The solution is administered, i.v., to a patient at a rate of ca. 1 liter per day over a period of several days to provide the patient's nitrogen requirements.

In the composition of Example V, the protein hydrolysate is replaced by an equivalent amount of a mixture comprising nutritionally-adequate amounts of all of the well-known essential amino acids, and equivalent results are secured.

The composition of Example V is modified by replacing the sodium n-octanoate with the following, respective, free carboxylic acids, at the concentrations indicated: n-butyric acid (0.4 molar); n-pentanoic acid (0.11 molar); n-hexanoic acid (30 millimolar); n-heptanoic acid (9 millimolar) and n-nonanoic acid (1 millimolar). The solution retains its sterility under hospital use conditions.

EXAMPLE VI

The total parenteral nutrition of a human or lower animal is carried out as follows.

A sterile dextrose solution is prepared in the manner of Example I, herein, with the deletion of the n-octanoic acid.

A separately-packaged, sterile solution of protein hydrolysate is prepared in the manner of Example V, herein, with the deletion of the n-octanoate material.

A separately-packaged, sterile aqueous solution comprising 0.6% by weight of sodium n-octanoate, adjusted to pH 4.8 with phosphate buffer, is prepared.

Individual containers of the three separate sterile solutions prepared in the foregoing manner are assembled on a rack and are directed, downwardly, through three separate sections of sterile tubing to a mixing chamber at the juncture of the tubing. The flow rate of the three individual solutions is adjusted so that they meet in the mixing chamber at a volume ratio of about 1:1:1. The solutions mix on passage through the mixing chamber and are transported therefrom by means of a single tube into the vein of the patient undergoing treatment.

Patients treated in the foregoing manner are less susceptible to mycotic and bacterial infections caused by seepage or spillage of the mixed dextrose and protein hydrolysate solutions at the point of entry into the vein than similar patients fed intravenously in the absence of the n-octanoate.

EXAMPLE VII

Sterile saline solutions (0.1%–20% NaCl) are prepared from NaCl and pyrogen-free water. Sterility is maintained (pH 5.0) with 0.065% n-octanoic acid and 1.0% n-hexanoic acid, respectively.

Sterile electrolyte solutions prepared in the manner of Example VIII are suitable for use as irrigation solutions and in kidney dialysis machines.

Sterile sodium acetate, sodium lactate and sodium phosphate (all 0.1%–25%) solutions are prepared in like fashion.

EXAMPLE VIII

In a convenient mode, the present invention is carried out by injecting the antifungal/antibacterial agents of the present type into commercially-available i.v. nutrient and/or saline solutions prior to use.

Sterile glass syringes, pre-fitted with hypodermic needles, are filled with unit doses (1.2 g in 15 g sterile $H_2O$) of sodium n-octanoate. The syringes are packaged under sterile conditions until time of use.

One-liter i.v. bottles of commercial dextrose solution, protein hydrolysate and physiological saline, respectively, all at pH 5.0, are artificially inoculated with strains of streptococcal bacteria and/or C. albicans to mimic the accidental contamination of i.v. solutions which might occur, undetected, under usage conditions. A one unit dose of the n-octanoate is injected through the rubber septum of each artificially contaminated i.v. solution. Excellent antimycotic/antibacterial activity is quickly obtained after injection of the n-octanoate into the contaminated i.v. bottles and the i.v. solutions are rendered non-infectious.

EXAMPLE IX

Nutritive solutions containing albumin-type proteins as a nutritive substance can be stabilized in the manner of the present invention. However, it has been discovered that the albumin proteins can interact with the carboxylic acid antimicrobial agents used in the manner of the present invention and inactivate them. Experiments have shown that one molecule of albumin can interact with, and inactivate, approximately ten molecules of carboxylic acid antimicrobial agent. Accordingly, when stabilizing nutritive compositions containing albumin, it is a simple matter to adjust the usage concentrations of the various carboxylic acid antimicrobials herein to account for the fact that approximately six moles of the carboxylate will be inactivated by each mole of albumin present in the nutritive composition. The following illustrates this technique.

A sterile, aqueous solution comprising 0.001 moles of bovine serum albumin in 1,000 ml. of water is prepared. The solution is buffered with a sodium acetate/acetic acid buffer and is made 0.010 molar in n-octanoic acid.

A solution of albumin and octanoic acid prepared in the foregoing manner does not exhibit good antimicrobial activity using the test criteria disclosed herein. However, when an additional three millimoles of n-octanoic acid are added to the solution following addition of the original portion of octanoic acid, excellent antimicrobial activity is secured. It is concluded that the original octanoic acid was bound by the albumin, and once the binding sites on the albumin are filled by the original octanoic acid, the remaining octanoic acid was free to provide the desired antimicrobial activity.

EXAMPLE X

An amino acid nutritive composition comprising soybean protein hydrolysate (5%), sodium chloride (1%) and pyrogen-free water is buffered to a pH in the range between 5–6 using an acetate buffer. The nutritive solution is stabilized by the presence of the following straight-chain carboxylic acids used at the concentrations indicated: 3-pentenoic acid (0.11 molar); 3-hexenoic acid (30 mM); 5-heptenoic acid (9 mM); 3-nonenoic acid (5 mM). The following branched-chain acids are used, respectively, to stabilize the solution: 2-methyl butyric acid (0.1 molar); 3-methyl hexanoic acid (30 mM); 3-ethyl nonanoic acid (10 mM). In like fashion, unsaturated analogs of n-octanoic acid can be used at concentrations in the range of about 3 millimolar, and higher, to maintain sterility in intravenous nutrient solutions and electrolyte solutions. Examples of such compounds include 2-octenoic acid, 3-octenoic acid and 4-octenoic acid.

As can be seen from the foregoing, total parenteral nutrition can now be achieved using compositions which comprise a nutritive amount of an amino acid source, sugar (dextrose), vitamins and minerals dissolved or dispersed in pyrogen-free water and stabilized against microbial contamination at physiological pH's with the disclosed carboxylic acids, especially n-octanoic acid.

What is claimed is:

1. In a process for the administration of a nutritive or saline solution or dispersion intravenously to a human or lower animal, the improvement which comprises admixing therewith at pH 3.5 to 6.0 a safe and effective amount of n-hexanoic acid, n-octanoic acid or a pharmaceutically-acceptable, water-soluble salt thereof, prior to or concurrently with said administration, whereby substantially all microorganisms known to be associated with infusion-related septicemia are killed within 1 minute of contact a decreased incidence of mycotic and bacterial infection is secured.

2. The process of claim 1 wherein the nutritive or saline solution or dispersion is admixed with n-octanoic acid or a pharmaceutically-acceptable, water-soluble salt thereof in an amount such that the solution or dispersion contains at least about a 3 millimolar, concentration of n-octanoic acid.

* * * * *

UNITED STATES PATENT AND TRADEMARK OFFICE
CERTIFICATE OF CORRECTION

PATENT NO. : 4,489,097
DATED : December 18, 1984
INVENTOR(S) : Roger L. Stone

It is certified that error appears in the above-identified patent and that said Letters Patent are hereby corrected as shown below:

Col. 16, line 30, "contact" should be -- contact and --.

Signed and Sealed this

Tenth Day of December 1985

[SEAL]

Attest:

Attesting Officer

DONALD J. QUIGG

Commissioner of Patents and Trademarks